United States Patent [19]

Kwon et al.

[11] Patent Number: 4,908,212

[45] Date of Patent: Mar. 13, 1990

[54] CHEWING GUM DESIGNED TO PREVENT TOOTH DECAY BY BLENDING A SOLUBLE EXTRACT OF CACAO BEAN HUSK

[75] Inventors: Ik B. Kwon; Hyung H. Park, both of Seoul; Bong J. An, Kyungpuk, all of Rep. of Korea

[73] Assignee: Lotte Confectionery Co., Ltd., Seoul, Rep. of Korea

[21] Appl. No.: 296,998

[22] Filed: Jan. 13, 1989

[30] Foreign Application Priority Data

Nov. 10, 1988 [KR] Rep. of Korea ............... 1988-14761

[51] Int. Cl.$^4$ ............................................. A61G 47/00
[52] U.S. Cl. ................... 424/440; 424/195.1; 424/49; 426/3
[58] Field of Search ............ 424/440, 48, 49, 195.1; 426/3, 655

[56] References Cited

U.S. PATENT DOCUMENTS 4,322,444 3/1982 Zuilichgm et al. ............... 426/482
4,532,147 7/1985 Jonas et al. ....................... 426/655

*Primary Examiner*—Ellis P. Robinson
*Assistant Examiner*—P. L. Prater
*Attorney, Agent, or Firm*—Armstrong, Nikaido Marmelstein, Kubovick & Murray

[57] ABSTRACT

Chewing gum designed to prevent tooth decay, for which a cacao bean husk is extracted by adding water or ethyl alcohol and an extract which is freeze dried after solvent is collected and concentrated by vacuum evaporation is added to the known raw materials of chewing gum in the ratio of 0.1–1.0%.

1 Claim, No Drawings

CHEWING GUM DESIGNED TO PREVENT TOOTH DECAY BY BLENDING A SOLUBLE EXTRACT OF CACAO BEAN HUSK

DETAILED DESCRIPTION OF THE INVENTION

The present invention relates to chewing gum blended of an extract of cacao bean husk. More particularly, it relates to chewing gum blended of a soluble extract of cacao bean husk gifted with a biologically active function for the prevention of tooth decay by blocking the synthesis of insoluble glucan (plaque).

Recently, decayed teeth are increasing in number due to excessive ingestion of sugar in particular.

The major cause of decayed teeth is that glucan is created from sugar by the bacteria existent in the oral cavity and it forms plaque by being attached to the surface of tooth. Thus, teeth are decayed by those bacteria based on such plaque.

In order to prevent teeth from decaying, dextranase and mutanase are used as enzymes which decompose glucan. In the chewing gum industry, tooth decay prevention chewing gum is now tested. For example, chewing gum in which sugar is replaced by other sweetening materials and chewing gum in which dextranase and mutanase are blended are now produced.

Recently, however, mutastein, which is a biologically active substance to inhibit the glucan synthesis from sugar by *Streptococcus mutans* which is bacteria existent in the oral cavity, has been found (Japanese Patent Publication 57-146587) and tooth decay prevention by a function dissimilar to the existing method is now watched.

The present inventors checked on the efficacy of cacao (*Theobroma cacao*) bean husk which is wasted in most cases, though its seeds are used all over the world as raw materials of chocolates. As a result, it was found that a soluble extract of cacao bean husk is gifted with a remarkable tooth decay prevention function. Thus, the present invention is brought to perfection by blending into chewing gum an extract which inhibits the glucan synthesis.

Accordingly, the object of the present invention is to provide chewing gum blended of a soluble extract of cacao bean husk gifted with a tooth decay prevention function.

The extract of cacao bean husk used in the present invention is obtained when a dried cacao bean husk is ground minutely and extracted in a normal way by adding water or ethyl alcohol and it is freeze-dried after collecting solution from it and concentrating it by vacuum evaporation.

The intended chewing gum is obtained by adding an extract of cacao bean husk together with spices in a normal way.

Additives include an extract of water, an extract of ethyl alcohol, a precipitate of ethyl alcohol and a precipitate of ammonium sulfate.

Each additive is added to chewing gum in the ratio of 0.1–1.0%.

Giving an explanation of the present invention according to its embodiments, it is as follows:

FIRST PROCESS (Embodiment 1)

After 20 g of completely dried cacao bean husk is ground minutely, 1 liter of water is added thereto and it is heated in 80° C. water for 30 minutes. Then, an extract obtained by repeating it three times is filtered. Thereafter, it is concentrated by vacuum evaporation. Then, it is freeze dried.

An extract amounts to 22% of the dried cacao bean husk.

FIRST PROCESS (Embodiment 2)

After 20 g of completely dried cacao bean husk is ground minutely, its fatty components are removed by adding 500 ml of hexane and a mixture of water and ethyl alcohol (50:50) is put in it. Then, it is continuously and discontinuously extracted for 2 hours at the normal temperature. As in Embodiment 1, the whole extract is filtered.

After it is concentrated by vacuum evaporation, it is freeze dried.

An extract amounts to about 27% of the dried cacao bean husk.

SECOND PROCESS (Embodiment 1)

After the powder (10 g) of an extract obtained by Embodiment 1 under the first process is dissolved completely in 500 ml of distilled water, a precipitate obtained by adding cooled ethyl alcohol 2.5 times as much as above mixture is collected by centrifugation. Then, it is freeze dried.

SECOND PROCESS (Embodiment 2)

After a precipitate obtained by adding 60% of ammonium sulfate (($NH_4$)$_2SO_4$) instead of ethyl acohol in Embodiment 1 under the second process is collected by centrifugation and dissolved in 50 ml of distilled water, its salt is removed by dialysis. Then, it is freeze dried.

A test for detection of the inhibitory activities of the insoluble glucan of each extract An extract of each embodiment under each process is diluted in distilled water so as to amount to 10% in concentration. Dilution is repeated by way of various concentrations for use as test samples for detection of the inhibitory activities of the insoluble glucan synthesis. Then, the extent to which the synthesis of insoluble glucan by glucosyltransferase with sucrose as a substrate is blocked is investigated.

For a test of detection of the inhibitory activities of the insoluble glucan synthesis, 0.8 ml of 1.25% sucrose solution (0.0025% sodium azide contained) prepared with a buffer solution (pH 6.5) of 65 mM calcium phosphate, 0.02 ml of glucosyltransferase and 0.18 ml of diluent of above extract are put into a test tube. After it is mixed well, it is made to react at 37° C. for 16 hours by giving a slope of 30 degrees. After reaction, the solution contained in the test tube is thrown away and glucan attached to the surface of its wall is cleaned with distilled water.

After glucan is made to disperse by adding 3 ml of distilled water and by using an ultrasonicator, the absorbance at 550 nm is measured with a spectrophotometer. Results are shown in Table 1.

Control is same as those used in the above testing method, but 0.18 ml of distilled water is added instead of a diluent of extract.

TABLE 1

| Extract (0.2%) | Absorbance at 550 nm |
|---|---|
| No addition | 1.558 |
| Embodiment 1 uder 1st process | 0.022 |
| Embodiment 2 under 1st process | 0.018 |
| Embodiment 1 under 2nd process | 0.048 |
| Embodiment 2 under 2nd process | 0.084 |

The embodiment in which gum is manufactured with an extract obtained in such a manner as described hereinabove is as follows:

| (Embodiment 1) | |
|---|---|
| Gum base | 20–30% |
| Palatinose | 62% |
| Sorbitol | 6% |
| Copper chlorophyll | 0.007% |
| Peppermint flavor | 2.47% |
| An extract of embodiment 1 under 1st process | 0.2% |

When the above materials are used in manufacturing chewing gum in a normal way, it is remarkably efficacious in blocking the insoluble glucan synthesis.

| (Embodiment 2) | |
|---|---|
| Gum base | 20–30% |
| Sorbitol | 68% |
| Copper chlorophyll | 0.007% |
| Peppermint flavor | 2.47% |
| An extract of embodiment 1 under 1st process | 0.2% |

Chewing gum provided with power to block the insoluble glucan synthesis is manufactured with above stated raw materials.

| (Embodiment 3) | |
|---|---|
| Gum base | 20–30% |
| Sorbitol | 5.8% |
| Sucrose | 62% |
| Copper chlorophyll | 0.007% |
| Peppermint flavor | 2.47% |
| An extract of embodiment 1 under 1st process | 0.2% |

Chewing gum provided with power to block the insoluble glucan synthesis is manufactured with above stated materials.

| (Embodiment 4) | |
|---|---|
| Gum base | 20–30% |
| Palatinose | 29% |
| Sorbitol | 38% |
| Copper chlorophyll | 0.007% |
| Peppermint flavor | 2.47% |
| An extract of embodiment 1 under 1st process | 0.2% |

Chewing gum provided with a remarkable medical virtues for the prevention of tooth decay is manufactured with raw materials listed above.

According to the present invention as described hereinabove, chewing gum can be provided by blending a soluble extract of cacao bean husk gifted with a new tooth decay prevention function. Thus, it not only provides a mellow falvor but also prevents tooth decay.

What is clamed is:

1. A chewing gum composition which aids in the prevention of tooth decay comprising the dried water soluble or ethanol soluble extract of cacao bean husk in the ratio of 0.1–1.0 weight percent of the composition, wherein said extract inhibits glucan synthesis.

* * * * *